United States Patent
Kondou et al.

(10) Patent No.: US 7,846,241 B2
(45) Date of Patent: Dec. 7, 2010

(54) PARTICULATE MATERIAL DETECTING APPARATUS

(75) Inventors: Atsuo Kondou, Okazaki (JP); Takeshi Sakuma, Nagoya (JP); Yasumasa Fujioka, Nagoya (JP)

(73) Assignee: NGK Insulators, Ltd., Nagoya (JP)

(*) Notice: Subject to any disclaimer, the term of this patent is extended or adjusted under 35 U.S.C. 154(b) by 0 days.

(21) Appl. No.: 12/542,805

(22) Filed: Aug. 18, 2009

(65) Prior Publication Data

US 2009/0308251 A1 Dec. 17, 2009

Related U.S. Application Data

(63) Continuation of application No. PCT/JP2008/053539, filed on Feb. 28, 2008.

(30) Foreign Application Priority Data

Mar. 15, 2007 (JP) .............................. 2007-066675

(51) Int. Cl.
 *B03C 3/12* (2006.01)
 *B03C 3/68* (2006.01)
(52) U.S. Cl. .................... 96/19; 96/62; 96/77; 96/95; 96/98
(58) Field of Classification Search .............. 96/19, 96/26, 60, 62, 77–79, 95, 98
See application file for complete search history.

(56) References Cited

U.S. PATENT DOCUMENTS

| | | | | |
|---|---|---|---|---|
| 4,376,637 A * | 3/1983 | Yang | ............................... | 95/74 |
| 4,498,338 A | 2/1985 | Peltonen et al. | | |
| 6,056,808 A * | 5/2000 | Krause | ............................... | 96/24 |
| 6,312,507 B1 * | 11/2001 | Taylor et al. | ............................... | 96/19 |
| 6,951,582 B1 * | 10/2005 | Tsai et al. | ............................... | 96/18 |
| 6,986,803 B1 * | 1/2006 | Richards | ............................... | 95/71 |
| 2005/0081719 A1 * | 4/2005 | Carlsson | ............................... | 96/223 |
| 2005/0231884 A1 | 10/2005 | Miyaishi et al. | | |
| 2006/0016336 A1 * | 1/2006 | Taylor et al. | ............................... | 96/25 |
| 2006/0024198 A1 | 2/2006 | Park et al. | | |

FOREIGN PATENT DOCUMENTS

| | | |
|---|---|---|
| GB | 2 211 618 | 7/1989 |
| JP | 58-137744 | 8/1983 |
| JP | 60-123761 | 7/1985 |
| JP | 60-228756 A * | 11/1985 |

(Continued)

*Primary Examiner*—Richard L Chiesa
(74) *Attorney, Agent, or Firm*—Burr & Brown

(57) ABSTRACT

A particulate matter detecting apparatus (100) includes a detecting apparatus main body having a cavity (2) that is formed through the detecting apparatus main body, a particle charging section (3) that can charge particulate matter that has entered the cavity through an inflow-side end (6) of the cavity, a collection section (4) that can collect the particulate matter charged by the particle charging section (3) and measure the amount of the particulate matter, and an ion wind generation section (5) that allows the particulate matter charged by the particle charging section (3) to flow toward an outflow-side end (7) of the cavity, the particle charging section, the collection section (4), and the ion wind generation section (5) being provided inside the cavity in this order from the inflow-side end (6). The particulate matter detecting apparatus has a reduced size, shows only a small measurement error, and can be produced inexpensively.

19 Claims, 5 Drawing Sheets

FOREIGN PATENT DOCUMENTS

| | | |
|---|---|---|
| JP | 1-203958 | 8/1989 |
| JP | 02-016445 | 1/1990 |
| JP | 11-276928 | 10/1999 |
| JP | 2003-154289 | 5/2003 |
| JP | 2003-275618 | 9/2003 |
| JP | 2005-518931 | 6/2005 |
| JP | 2005-209600 | 8/2005 |
| JP | 2006-0034957 | 2/2006 |
| WO | 03/074184 A1 | 9/2003 |

\* cited by examiner

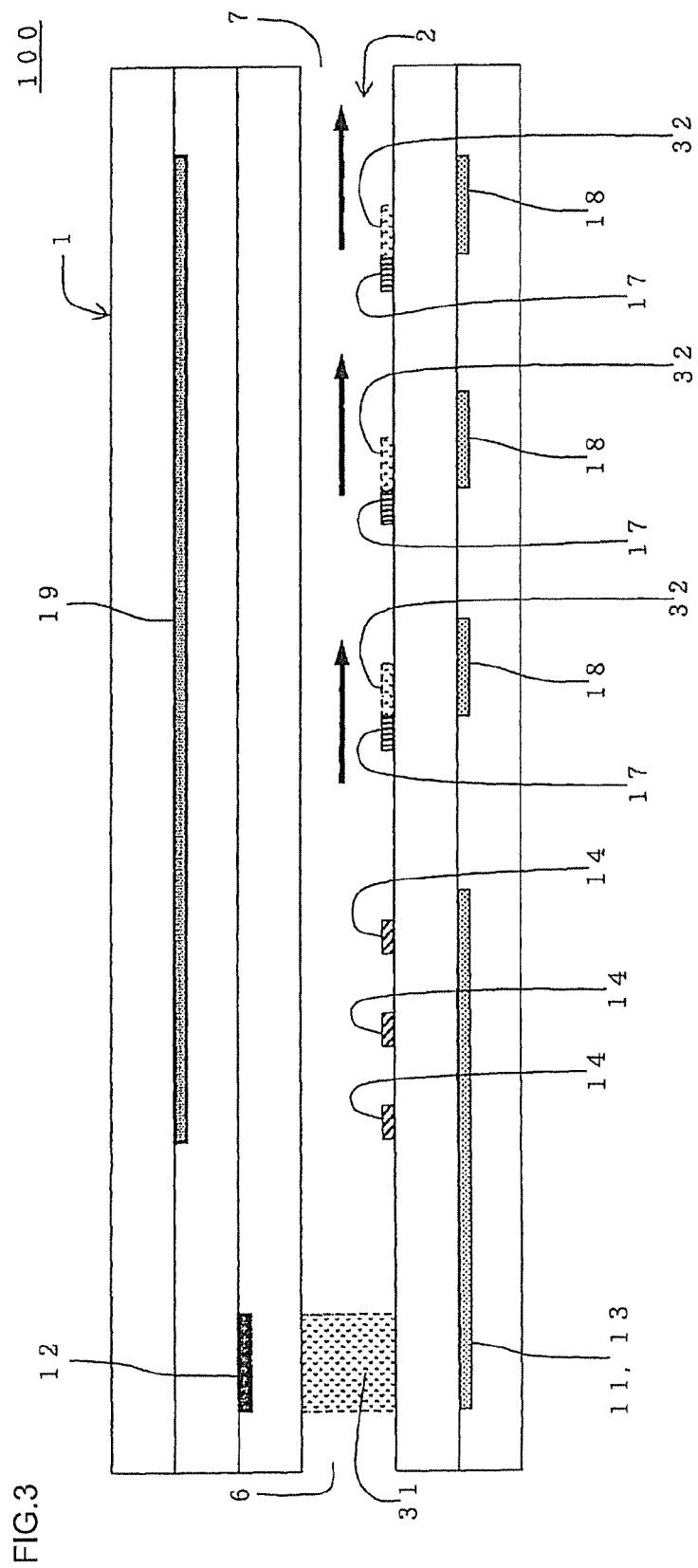

PARTICULATE MATERIAL DETECTING APPARATUS

FIELD OF THE INVENTION

The present invention relates to a particulate matter detecting apparatus. More particularly, the present invention relates to a particulate matter detecting apparatus that has a reduced size, shows only a small measurement error, and can be produced inexpensively.

BACKGROUND OF THE INVENTION

A flue gas or a diesel engine exhaust gas contains particulate matter (PM) (e.g., soot) that causes air pollution. A filter (diesel particulate filter (DPF)) formed of a ceramic or the like has been widely used to remove particulate matter. A DPF formed of a ceramic can be used for a long period of time, but may suffer defects (e.g., cracks or erosion) due to thermal deterioration or the like so that a small amount of particulate matter may leak from the DPF. It is very important to immediately detect such defects (i.e., abnormality) from the viewpoint of preventing air pollution.

As a method of detecting such defects, a particulate matter detecting apparatus may be provided on the downstream side of a DPF (see Patent Document 1, for example).

Patent Document 1: JP-A-60-123761

SUMMARY OF THE INVENTION

According to the invention disclosed in Patent Document 1, particulate matter is charged by causing a corona discharge, and an ion current due to the particulate matter is measured to determine the amount of the particulate matter. According to this method, since the ion current due to the particulate matter is weak, a large-scale detection circuit is required to detect such a weak ion current so that cost increases. Moreover, since the particulate matter cannot be effectively charged when the exhaust gas flows at a high flow rate, the amount of particulate matter measured may be smaller than the amount of particulate matter actually contained in the exhaust gas (i.e., a large error may occur).

The present invention was conceived in view of the above problems. An object of the present invention is to provide a particulate matter detecting apparatus that has a reduced size, shows only a small measurement error, and can be produced inexpensively.

In order to achieve the above object, the present invention provides the following particulate matter detecting apparatus.

A particulate matter detecting apparatus that includes a detecting apparatus main body having a cavity that is formed through the detecting apparatus main body; a particle charging section that can charge particulate matter that has entered the cavity through one end (inflow-side end) of the cavity; a collection section that can collect the particulate matter charged by the particle charging section and measure the amount of the particulate matter; and an ion wind generation section that allows the particulate matter charged by the particle charging section to flow toward the other end (outflow-side end) of the cavity, the particle charging section, the collection section, and the ion wind generation section being provided inside the cavity in this order from the inflow-side end.

The particulate matter detecting apparatus, wherein the detecting apparatus main body preferably includes a charging electrode and a ground electrode (charging ground electrode) that are disposed so that the particle charging section provided inside the cavity is positioned between the charging electrode and the ground electrode; and wherein the particle charging section charges the particulate matter via a silent discharge that is generated inside the cavity using the charging electrode.

The particulate matter detecting apparatus, wherein the detecting apparatus main body preferably further includes a charging electrode and a ground electrode (charging ground electrode) that are disposed so that the particle charging section provided inside the cavity is positioned between the charging electrode and the ground electrode; and wherein the particle charging section charges the particulate matter via a corona discharge that is generated inside the cavity using the charging electrode.

The particulate matter detecting apparatus, wherein the charging electrode and the charging ground electrode preferably contain at least one component selected from the group consisting of gold, silver, platinum, nickel, molybdenum, and tungsten.

The particulate matter detecting apparatus, wherein the collection section preferably includes a collection electrode that can electrostatically collect the particulate matter charged by the particle charging section and is disposed on an inner wall surface of the cavity.

The particulate matter detecting apparatus, wherein the collection electrode is preferably included in the collection section is a plate-shaped electrode that has an external profile provided with elevations or depressions.

The particulate matter detecting apparatus, wherein the collection electrode preferably contains at least one component selected from the group consisting of gold, silver, platinum, nickel, molybdenum, and tungsten.

The particulate matter detecting apparatus, that further includes a ground electrode (collection ground electrode) that is disposed inside a wall that forms the inner wall surface of the cavity on which the collection electrode is disposed, the particulate matter detecting apparatus being capable of measuring the amount of the particulate matter collected by the collection electrode by detecting a change in capacitance between the collection electrode and the collection ground electrode.

The particulate matter detecting apparatus, wherein the collection ground electrode preferably contains at least one component selected from the group consisting of gold, silver, platinum, nickel, molybdenum, and tungsten.

The particulate matter detecting apparatus, that further includes at least one electrode extension portion that is disposed in the inner wall surface of the collection section on which the collection electrode is disposed so as not to come in contact with the collection electrode, wherein the collection electrode and the electrode extension portion are electrically connected when the particulate matter collected by the collection electrode has accumulated between the collection electrode and the electrode extension portion.

The particulate matter detecting apparatus, that preferably includes a plurality of the electrode extension portions, wherein the plurality of electrode extension portions differ in the distance from the collection electrode.

The particulate matter detecting apparatus, wherein the ion wind generation section preferably includes an ion wind generation electrode on the inner wall surface of the cavity, the ion wind generation electrode causing a surface discharge so that the particulate matter charged by the particle charging section moves toward the outflow-side end.

The particulate matter detecting apparatus, wherein the ion wind generation section preferably includes an ion wind generation electrode on the inner wall surface of the cavity, the ion wind generation electrode causing a corona discharge so that the particulate matter charged by the particle charging section moves toward the outflow-side end.

The particulate matter detecting apparatus, wherein the ion wind generation electrode preferably contains at least one component selected from the group consisting of gold, silver, platinum, nickel, molybdenum, stainless steel, and tungsten.

The particulate matter detecting apparatus wherein a material that forms the detecting apparatus main body is preferably a ceramic.

The particulate matter detecting apparatus, wherein the detecting apparatus main body is preferably formed by stacking a plurality of ceramic tapes.

The particulate matter detecting apparatus, wherein the ceramic that forms the detecting apparatus main body preferably contains at least one component selected from the group consisting of alumina, magnesium oxide, silicon oxide, silicon nitride, aluminum nitride, zirconia, cordierite, mullite, spinel, a magnesium-calcium-titanium oxide, a barium-titanium-zinc oxide, and a barium-titanium oxide.

The particulate matter detecting apparatus, wherein the detecting apparatus main body preferably includes a purification electrode and a ground electrode (purification ground electrode) that are disposed so that the cavity is positioned between the purification electrode and the purification ground electrode, and a silent discharge can be generated inside the cavity using the purification electrode and the purification ground electrode to remove the particulate matter that adheres to the inner wall surface of the cavity.

The particulate matter detecting apparatus, wherein the purification electrode and the purification ground electrode preferably contain at least one component selected from the group consisting of gold, silver, platinum, nickel, molybdenum, and tungsten.

The particulate matter detecting apparatus, wherein the particulate matter that passes through the cavity is preferably soot discharged from a diesel engine or nanoparticles produced in a nanoparticle production plant.

The particulate matter detecting apparatus according to the present invention allows particulate matter (exhaust gas) to enter the cavity that is formed through the detecting apparatus main body, and includes the particle charging section that can charge the particulate matter that has entered the cavity through one end (inflow-side end) of the cavity, the collection section that can collect the particulate matter charged by the particle charging section and measure the amount of the particulate matter, and the ion wind generation section that allows the particulate matter charged by the particle charging section to flow toward the other end (outflow-side end) of the cavity, the particle charging section, the collection section, and the ion wind generation section being provided inside the cavity in this order from the inflow-side end. Therefore, the amount of particulate matter contained in the entire exhaust gas can be calculated by measuring only the amount of particulate matter that has entered the cavity instead of directly measuring the entire particulate matter contained in the exhaust gas that flows on the downstream side of the DPF. As a result, the particulate matter detecting apparatus can be reduced in size and produced inexpensively. Even if the total flow rate of the exhaust gas that flows on the downstream side of the DPF is high, the ion wind generation section can draw part of the exhaust gas (particulate matter) into the cavity at a constant flow rate so that the particulate matter flows through the cavity. Therefore, the particulate matter inside the cavity can be entirely and effectively charged by the particle charging section so that a measured value with only a small error can be obtained. Moreover, even if the total flow rate of the exhaust gas that flows on the downstream side of the DPF changes, the amount of exhaust gas that flows through the cavity can be controlled independently of the total flow rate. Therefore, a measured value with only a small error can be obtained.

BRIEF DESCRIPTION OF THE DRAWINGS

FIG. 3 is a cross-sectional view along the line A-A' shown in FIG. 2A, and shows a discharge state.

EXPLANATION OF SYMBOLS

1: detecting apparatus main body, 2: cavity, 3: particle charging section, 4: collection section, 5: ion wind generation section, 6: inflow-side end, 7: outflow-side end, 11: ground electrode, 12: charging electrode, 13: charging ground electrode, 14: collection electrode, 15: collection ground electrode, 16, 16a, 16b, 16c: electrode extension portion, 17: ion wind generation electrode, 18: ion wind generation ground electrode, 19: purification electrode, 20: purification ground electrode, 21: collection electrode installation surface, 22: ground electrode installation wall, 31: charging surface discharge, 32: surface discharge, 33: plasma, 41: ceramic sheet, 100: particulate matter detecting apparatus, a, b, c: distance

BEST MODE FOR CARRYING OUT THE INVENTION

Embodiments of the present invention are described in detail below with reference to the drawings. Note that the present invention is not limited to the following embodiments. Various modifications, improvements, and the like may be appropriately made with regard to the design without departing from the scope of the present invention based on common knowledge of a person skilled in the art.

Figure 1:
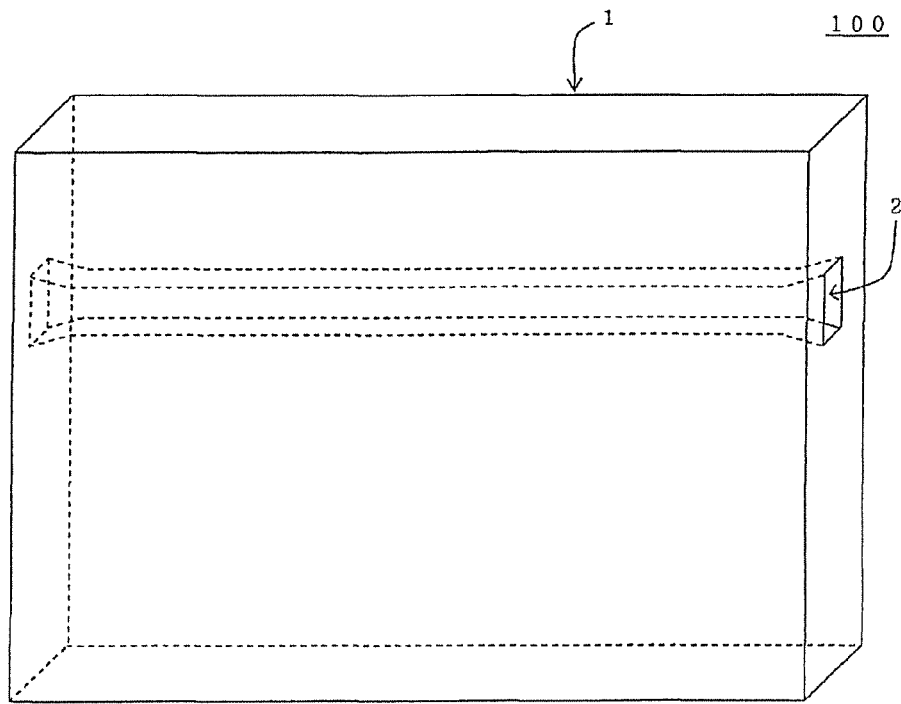
FIG. 1 is a perspective view schematically showing a particulate matter detecting apparatus according to one embodiment of the present invention.

FIG. 1 is a perspective view schematically showing a particulate matter detecting apparatus according to one embodiment of the present invention. As shown in FIG. 1, a particulate matter detecting apparatus 100 according to this embodiment includes a detecting apparatus main body 1 having a cavity 2 that is formed through the detecting apparatus main body 1. The cavity 2 allows particulate matter to pass through.

Figure 2A:
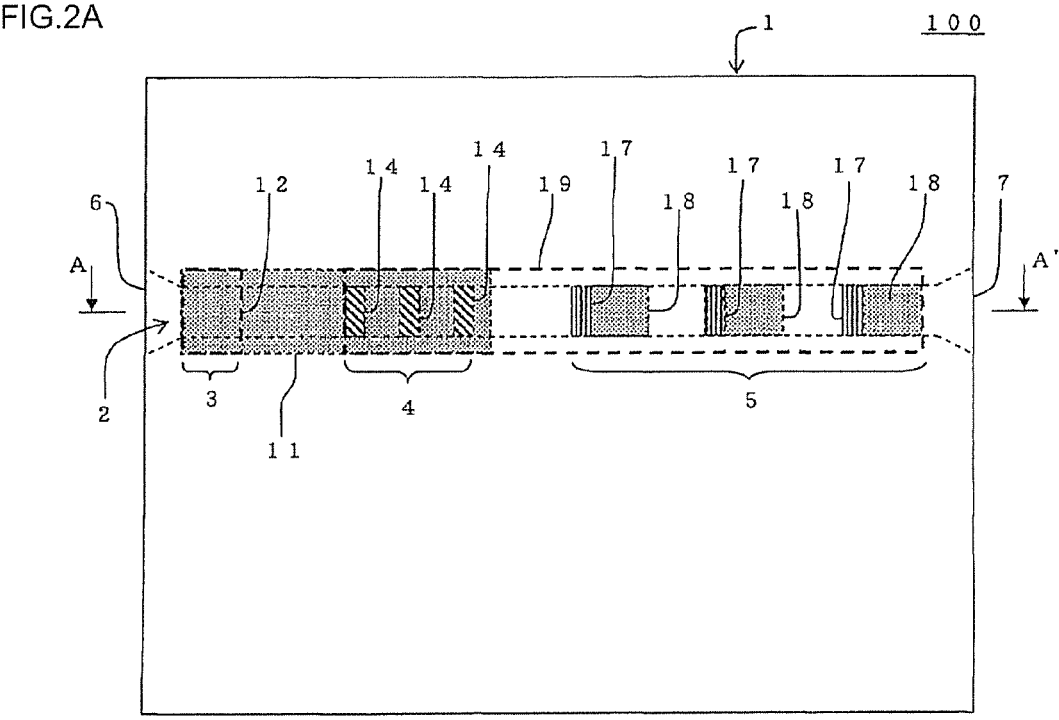
FIG. 2A is a side view schematically showing a particulate matter detecting apparatus according to one embodiment of the present invention.
Figure 2B:
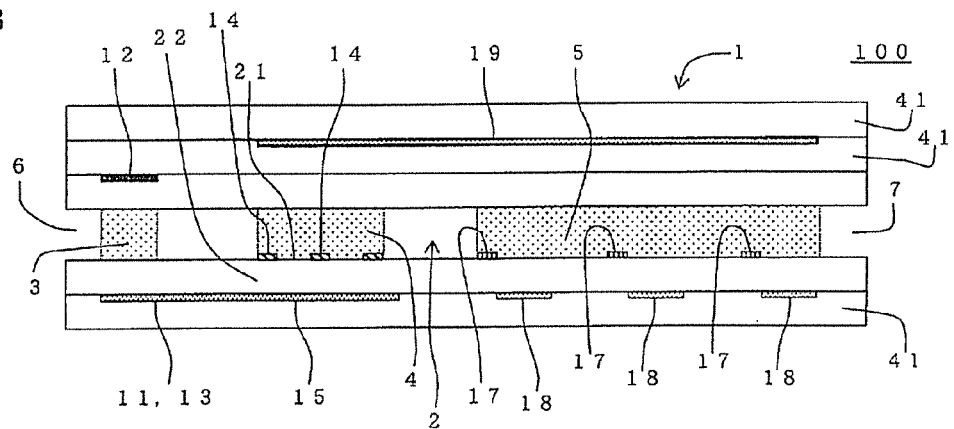
FIG. 2B is a cross-sectional view along the line A-A' shown in FIG. 2A.

FIGS. 2A and 2B schematically show the particulate matter detecting apparatus according to one embodiment of the present invention. FIG. 2A is a side view, and FIG. 2B is a cross-sectional view along the line A-A' shown in FIG. 2A. FIG. 2A is a side view showing the particulate matter detecting apparatus according to this embodiment shown in FIG. 1, and FIG. 2B is a cross-sectional view showing the particulate matter detecting apparatus according to this embodiment shown in FIG. 1. In FIG. 2A, the cavity 2 that is formed through the detecting apparatus main body 1 and a position where electrodes are disposed are indicated by broken lines for convenience. As shown in FIGS. 2A and 2B, the particulate matter detecting apparatus 100 according to this embodiment includes a particle charging section 3 that can charge particulate matter that has entered the cavity 2 through one end (inflow-side end) 6 of the cavity 2, a collection section 4 that can collect the particulate matter charged by the particle charging section 3 and measures the amount of the particulate matter, and an ion wind generation section 5 that allows an exhaust gas inside the cavity to flow toward the other end 7 of the cavity, the particle charging section 3, the collection section 4, and the ion wind generation section 5 being provided in the cavity 2 in this order from the inflow-side end 6.

Since the particulate matter detecting apparatus 100 according to this embodiment is configured so that the ion wind generation section 5 can generate an ion wind that flows from the inflow-side end 6 toward the outflow-side end 7 at a constant flow rate inside the cavity 2 such that a constant amount of exhaust gas can enter, pass through, and flow out from the cavity 2 and the amount of particulate matter contained in the entire exhaust gas can be calculated by measuring only the amount of particulate matter that has entered the cavity 2. Therefore, the particulate matter detecting apparatus can be reduced in size and produced inexpensively. Moreover, even if the total flow rate of the exhaust gas that flows on the downstream side of the DPF is high or changes, the ion wind generation section 5 can draw part of the exhaust gas (particulate matter) into the cavity at a constant flow rate so that the particulate matter flows through the cavity. Therefore, the particulate matter inside the cavity can be entirely and effectively charged by the particle charging section 3 so that a measured value with only a small error can be obtained by the collection section 4.

As shown in FIGS. 2A and 2B, the particulate matter detecting apparatus 100 according to this embodiment includes the particle charging section 3 that is provided inside the cavity 2 and positioned near the inflow-side end 6. The particle charging section 3 refers to an area that can charge particulate matter. It is preferable that the particle charging section 3 be disposed inside the cavity 2 within an area that corresponds to one-fourth of the total length of the cavity 2 (i.e., the distance between the inflow-side end 6 and the outflow-side end 7) from the inflow-side end 6 of the cavity 2.

As shown in FIG. 3, the particulate matter detecting apparatus 100 according to this embodiment is preferably configured so that the detecting apparatus main body 1 includes a charging electrode 12 and a ground electrode 11 (charging ground electrode 13) that are disposed so that the particle charging section 3 provided inside the cavity 2 is positioned between the charging electrode 12 and the ground electrode 11, and the particle charging section 3 charges the particulate matter via a silent discharge (charging silent discharge 31) that is generated inside the cavity 2 using the charging electrode 12. FIG. 3 is a cross-sectional view along the line A-A' shown in FIG. 2A, and shows a discharge state. Since the particulate matter contained in the exhaust gas that has entered the cavity 2 at a constant flow rate is charged by the charging surface discharge 31 inside the cavity 2, the particulate matter inside the cavity 2 can be efficiently charged.

A voltage applied between the charging electrode 12 and the charging ground electrode 13 is not particularly limited insofar as a silent discharge occurs but an arc discharge does not occur. The shape of the charging electrode 12 is not particularly limited. It is preferable that the charging electrode 12 be a rectangular film or sheet (see FIGS. 2A and 2B). Note that the charging electrode 12 may be a film or a sheet in the shape of a circle, an oval, a track, a polygon (e.g., pentagon), or the like. The thickness of the charging electrode 12 is not particularly limited insofar as the charging electrode 12 exhibits high durability during discharge and does not hinder the exhaust gas that has entered the cavity 2. The area of the charging electrode 12 is not particularly limited insofar as the charging electrode 12 can effectively charge the particulate matter that has entered the cavity 2 and does not unnecessarily require electric power when causing a silent discharge. As shown in FIG. 2A, it is preferable that the dimension (length) of the charging electrode 12 in the vertical direction in FIG. 2A (i.e., a direction that is perpendicular to the extension direction of the cavity 2 and is parallel to the charging electrode 12; this direction is referred to as the vertical direction of the detecting apparatus main body 1) be larger than the dimension of the cavity 2 in the vertical direction of the detecting apparatus main body 1 so that the charging electrode 12 covers the cavity 2 from the upper side to the lower side (when viewed from the side of the detecting apparatus main body 1).

It is preferable that the charging ground electrode 13 have a size equal to or larger than that of the charging electrode 12. It is preferable that the charging ground electrode 13 be disposed at such a position that the charging electrode 12 overlaps (faces) the charging ground electrode 13 when moving the charging electrode 12 in the direction (normal direction) perpendicular to the surface of the charging electrode 12. As shown in FIGS. 2A and 2B, it is preferable that the charging ground electrode 13 be a rectangular film or sheet. Note that the charging ground electrode 13 may be a film or a sheet in the shape of a circle, an oval, a track, a polygon (e.g., pentagon), or the like. As shown in FIGS. 2A and 2B, it is preferable that the charging ground electrode 13 and a collection ground electrode 15 (ground electrode 11) be a common electrode. Note that the charging ground electrode 13 and the collection ground electrode 15 may be separated. The thickness of the charging ground electrode 13 is not particularly limited insofar as the charging ground electrode 13 forms a continuous conductor film. The area of the charging ground electrode 13 is not particularly limited insofar as the charging section and the collection section are located at a moderate distance to ensure an accurate measurement and an increase in cost due to an increase in size of the entire element does not occur. As shown in FIG. 2A, it is preferable that the upper end and the lower end of the charging ground electrode 13 in the vertical direction of the detecting apparatus main body 1 overlap the charging electrode 12 (when viewed from the side of the detecting apparatus main body 1).

In the particulate matter detecting apparatus 100 according to this embodiment, it is also preferable that the particle charging section 3 charge the particulate matter via a corona discharge that is generated inside the cavity 2 using the charging electrode 12. In this case, it is preferable that the charging electrode 12 have a sharp end (e.g., needle-like electrode) that protrudes into the cavity 2. When causing a corona discharge, a voltage applied between the charging electrode 12 and the charging ground electrode 13 is not particularly limited insofar as a corona discharge occurs but an arc discharge does not occur.

In the particulate matter detecting apparatus 100 according to this embodiment, it is preferable that the collection section 4 include a collection electrode 14 that can electrostatically collect the particulate matter charged by the particle charging section 3 on the inner wall surface of the cavity 2. The collection section 4 refers to an area that can electrostatically collect the particulate matter. It is preferable that the collection section 4 be disposed inside the cavity 2 within an area that corresponds to one-eighth to seven-eighth of the total length of the cavity 2 (i.e., the distance between the inflow-side end 6 and the outflow-side end 7) from the inflow-side end 6 of the cavity 2.

It is preferable that the particulate matter detecting apparatus 100 include the ground electrode 11 (collection ground electrode 15) that is disposed inside a wall (ground electrode installation wall 22) that forms the inner wall surface (collection electrode installation surface 21) of the cavity 2 on which the collection electrode 14 is disposed, and measure the amount of particulate matter collected by the collection electrode 14 by detecting a change in capacitance between the collection electrode 14 and the collection ground electrode 15.

Since the particulate matter detecting apparatus 100 can measure the amount of particulate matter collected by the collection electrode 14 by detecting a change in capacitance between the collection electrode 14 and the collection ground electrode 15, the circuit scale of a detection circuit can be reduced so that the size of the particulate matter detecting apparatus 100 can be further reduced. Furthermore, the particulate matter detecting apparatus 100 can be produced more inexpensively.

A voltage applied between the collection electrode 14 and the collection ground electrode 15 is preferably determined so that an inter-electrode dielectric breakdown or a leakage current that leaks to a peripheral conductor does not occur to a large extent. The voltage applied between the collection electrode 14 and the collection ground electrode 15 is more preferably –30 to 30 V that allows utilization of a general-purpose IC. The distance between the collection electrode 14 and the collection ground electrode 15 is not particularly limited insofar as an initial variation in capacitance due to a production variation does not occur to a large extent, and a change in capacitance when soot has been collected is sufficiently large so that the sensitivity does not decrease.

Figure 4A:
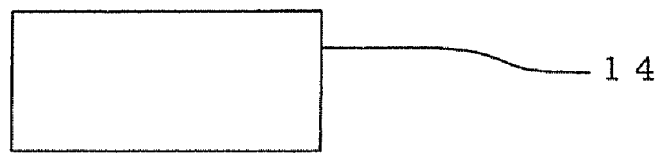
FIG. 4A is a plan view schematically showing the shape of a collection electrode.
Figure 4B:
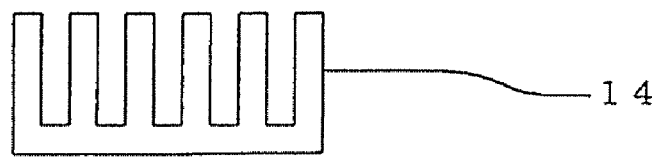
FIG. 4B is a plan view schematically showing the shape of a collection electrode.
Figure 4C:
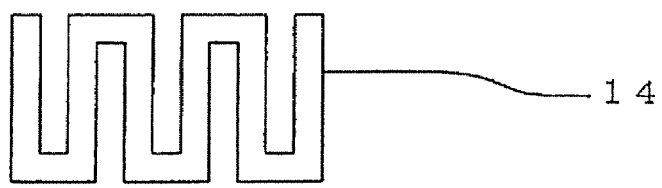
FIG. 4C is a plan view schematically showing the shape of a collection electrode.

The collection electrode 14 may be a plate-shaped electrode that has a rectangular external profile, as shown in FIG. 4A. Note that it is preferable that the collection electrode 14 be a plate-shaped electrode that has an external profile provided with elevations or depressions, as shown in FIGS. 4B and 4C. Note that the expression "provided with elevations or depressions" used herein refers to a case where the external profile is provided with both elevations and depressions, a case where the external profile is provided with only depressions, and a case where the external profile is provided with only elevations. FIGS. 4A, 4B, and 4C are plan views schematically showing the collection electrode 14. The collection electrode 14 shown in FIG. 4B differs from the rectangular collection electrode 14 shown in FIG. 4A in that one side of the collection electrode 14 is provided with a plurality of depressions and elevations. In other words, a plurality of comb-shaped elevations are formed in FIG. 4B. Specifically, the terms "depression" and "elevation" may be interchangeably used. Such a case is also included within the scope of the expression "provided with elevations or depressions." The collection electrode 14 shown in FIG. 4C differs from the rectangular collection electrode 14 shown in FIG. 4B in that two parallel sides of the collection electrode 14 are alternately provided with a plurality of depressions.

The thickness of the collection electrode 14 is not particularly limited insofar as the collection electrode 14 exhibits high durability and does not hinder the exhaust gas that has entered the cavity 2. The area of the collection electrode 14 is not particularly limited insofar as the capacitance sufficiently changes when soot has been collected, and electric power is not unnecessarily consumed when cleaning the adhering soot. The dimension of the collection electrode 14 in the vertical direction in FIG. 2A (i.e., the vertical direction of the detecting apparatus main body 1) is not particularly limited, but is preferably the same as the dimension of the cavity 2 in the vertical direction of the detecting apparatus main body 1, as shown in FIG. 2A. The number of collection electrodes 14 may be one or more. The number of collection electrodes 14 is preferably one to five.

It is preferable that the collection ground electrode 15 have a size equal to or larger than that of the collection electrode 14. It is preferable that the collection ground electrode 15 be disposed at such a position that the collection electrode 14 overlaps the collection ground electrode 15 when moving the collection electrode 14 in the direction (normal direction) perpendicular to the surface of the collection electrode 14. The collection ground electrode 15 and the charging ground electrode 13 are preferably formed by a common electrode, but may be separated. When the collection ground electrode 15 and the charging ground electrode 13 are formed by a common electrode, it is preferable that the collection ground electrode 15 be a rectangular film or sheet (see FIGS. 2A and 2B). Note that the collection ground electrode 15 may be a film or a sheet in the shape of a circle, an oval, a track, a polygon (e.g., pentagon), or the like. When the collection ground electrode 15 and the charging ground electrode 13 are separated, it is also preferable that the collection ground electrode 15 have the above-mentioned shape. The thickness of the collection ground electrode 15 is not particularly limited insofar as the collection ground electrode 15 forms a continuous conductor film.

Figure 5:
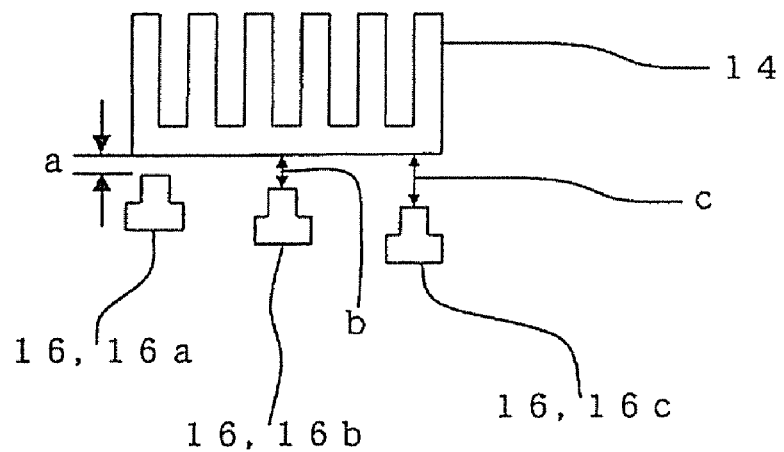
FIG. 5 is a plan view schematically showing a collection electrode and an electrode extension portion.

In the particulate matter detecting apparatus 100 according to this embodiment, it is preferable to dispose at least one electrode extension portion in the inner wall surface (collection electrode installation surface 21) of the collection section 4 on which the collection electrode 14 is disposed so as not to come in contact with the collection electrode 14. As shown in FIG. 5, it is more preferable to dispose a plurality of electrode extension portions 16 so as not to come in contact with the collection electrode 14, for example. It is preferable that the collection electrode 14 and the electrode extension portion 16 be electrically connected when the particulate matter collected by the collection electrode 14 has accumulated between the collection electrode 14 and the electrode extension portion 16. The capacitance between the collection electrode 14 and the collection ground electrode 15 gradually changes when the particulate matter is collected by the collection electrode 14 (i.e., when the collection electrode 14 and the electrode extension portion 16 are not electrically connected), and increases to a large extent when the collection electrode 14 and the electrode extension portion 16 are electrically connected so that it is possible to determine that a given amount of particulate matter has been collected. When a plurality of electrode extension portions 16 are disposed (see FIG. 5), it is preferable that the electrode extension portions 16 (16a, 16b, 16c) differ in the distance (a, b, c) from the collection electrode 14. The amount of particulate matter collected by the collection electrode 14 can be determined in a plurality of stages when the electrode extension portions 16

(16a, 16b, 16c) differ in the distance (a, b, c) from the collection electrode 14. In this case, the distances between the electrode extension portions 16 (16a, 16b, 16c) are not particularly limited. It is preferable that the distances between the electrode extension portions 16 (16a, 16b, 16c) be longer than the distance (a, b, c) from the collection electrode 14 to each electrode extension portion 16 (16a, 16b, 16c).

As shown in FIGS. 2A and 2B, the particulate matter detecting apparatus 100 according to this embodiment includes the ion wind generation section 5 that is disposed inside the cavity 2 at a position near the outflow-side end 7. The ion wind generation section 5 refers to an area that can discharge electricity for generating an ion wind. It is preferable that the ion wind generation section 5 be disposed inside the cavity 2 within an area that corresponds to $3/4$ to $49/50$ of the total length of the cavity 2 (i.e., the distance between the inflow-side end 6 and the outflow-side end 7) from the inflow-side end 6 of the cavity 2.

In the particulate matter detecting apparatus 100 according to this embodiment, as shown in FIGS. 2A, 2B, and 3, it is preferable that the ion wind generation section 5 include an ion wind generation electrode 17 on the inner wall surface of the cavity, the ion wind generation electrode 17 causing a surface discharge so that the exhaust gas containing the particulate matter charged by the particle charging section 3 moves toward the outflow-side end 7. It is preferable that the ion wind generation section 5 include an ion wind generation ground electrode 18 that is embedded in the wall that forms the inner wall surface of the cavity 2 on which the ion wind generation electrode 17 is disposed, and cause a surface discharge 32 upon application of a voltage between the ion wind generation electrode 17 and the ion wind generation ground electrode 18. It is preferable that the ion wind generation ground electrode 18 be positioned closer to the outflow-side end than the ion wind generation electrode 17, as shown in FIGS. 2A, 2B, and 3. Therefore, the surface discharge 32 occurs in the direction in which the cavity 2 extends (i.e., the lengthwise direction of the cavity 2) when applying a voltage between the ion wind generation electrode 17 and the ion wind generation ground electrode 18, and a force is applied to the charged particulate matter due to the surface discharge 32 in the direction toward the outflow-side end 7 so that an ion wind can be generated.

It is preferable that the volume of the ion wind be sufficient to measure the amount of soot contained in the exhaust gas and be controlled independently of the total flow rate of the exhaust gas.

It is preferable to determine the voltage applied between the ion wind generation electrode 17 and the ion wind generation ground electrode 18, the distance between the ion wind generation electrode 17 and the ion wind generation ground electrode 18, and the area of the ion wind generation electrode 17 so that a dielectric breakdown does not occur, an ion wind at a volume sufficient to measure the amount of soot contained in the exhaust gas can be generated, and the volume of the ion wind can be controlled independently of the total flow rate of the exhaust gas.

The thickness of the ion wind generation electrode 17 is not particularly limited insofar as the ion wind generation electrode 17 exhibits high durability during discharge and does not hinder the flow of the exhaust gas that has entered the cavity 2. The dimension of the ion wind generation electrode 17 in the vertical direction in FIG. 2A (i.e., the vertical direction of the detecting apparatus main body 1) is not particularly limited, but is preferably the same as the dimension of the cavity 2 in the vertical direction of the detecting apparatus main body 1, as shown in FIG. 2A. The number of ion wind generation electrodes 17 is not particularly limited, but is preferably one or more. The number of ion wind generation electrodes 17 is more preferably 2 to 100.

The shape of the ion wind generation electrode 17 is not particularly limited. As shown in FIGS. 2A and 2B, it is preferable that the ion wind generation electrode 17 be a rectangular film or sheet. Note that the ion wind generation electrode 17 may be a film or a sheet in the shape of a circle, an oval, a track, a polygon (e.g., pentagon), or the like.

It is preferable that the ion wind generation ground electrode 18 have a size equal to or larger than that of the ion wind generation electrode 17. As shown in FIGS. 2A, 2B, and 3, it is preferable that the ion wind generation ground electrode 18 be disposed at such a position that the end of the ion wind generation electrode 17 on the side of the outflow-side end 7 overlaps the end of the ion wind generation ground electrode 18 on the side of the inflow-side end 6 when moving the ion wind generation electrode 17 in the direction (normal direction) perpendicular to the surface of the ion wind generation electrode 17. As shown in FIGS. 2A and 2B, it is preferable that the ion wind generation ground electrode 18 be a rectangular film or sheet. Note that the ion wind generation ground electrode 18 may be a film or a sheet in the shape of a circle, an oval, a track, a polygon (e.g., pentagon), or the like. The thickness of the ion wind generation ground electrode 18 is not particularly limited insofar as the ion wind generation ground electrode 18 forms a continuous conductor film. The area of the ion wind generation ground electrode 18 is not particularly limited, but is preferably determined so that an ion wind at a volume sufficient to measure the amount of soot contained in the exhaust gas can be generated and the volume of the ion wind can be controlled independently of the total flow rate of the exhaust gas.

In the particulate matter detecting apparatus 100 according to this embodiment, it is also preferable that the ion wind generation section 5 include an ion wind generation electrode on the inner wall surface of the cavity 2, the ion wind generation electrode causing a corona discharge so that the exhaust gas containing the particulate matter charged by the particle charging section 3 moves toward the outflow-side end 7. In this case, it is preferable that the ion wind generation electrode have a sharp end (e.g., needle-like electrode) that protrudes into the cavity 2. A voltage applied between the ion wind generation electrode and the ion wind generation ground electrode 18 when causing a corona discharge is preferably determined so that an arc discharge does not occur, an ion wind at a volume sufficient to measure the amount of soot contained in the exhaust gas can be generated, and the volume of the ion wind can be controlled independently of the total flow rate of the exhaust gas.

It is preferable that the material for each of the ground electrode 11 (charging ground electrode 13, collection ground electrode 15, and ion wind generation ground electrode 18), the charging electrode 12, the collection electrode 14, the electrode extension portion 16, and the ion wind generation electrode 17 contain at least one component selected from the group consisting of gold, silver, platinum, nickel, molybdenum, stainless steel, and tungsten. The content of these components is preferably 20 vol % or more.

In the particulate matter detecting apparatus 100 according to this embodiment, the detecting apparatus main body 1 is a structure having a cavity that is formed through the detecting apparatus main body 1. The structure has a wall that surrounds the cavity in the shape of a tube. It is preferable that the material that forms the detecting apparatus main body 1 (structure) is a ceramic. It is more preferable that the material that forms the detecting apparatus main body 1 contain at least one component selected from the group consisting of alumina, magnesium oxide, silicon oxide, silicon nitride, aluminum nitride, zirconia, cordierite, mullite, spinel, a magnesium-calcium-titanium oxide, a barium-titanium-zinc oxide, and a barium-titanium oxide.

It is preferable that the detecting apparatus main body 1 be formed by stacking a plurality of ceramic tapes (ceramic sheets 41) (see FIGS. 2B and 3). In this case, since the detecting apparatus main body 1 can be formed by stacking a plurality of ceramic tapes while placing the electrodes between the ceramic tapes, the particulate matter detecting apparatus 100 according to this embodiment can be efficiently produced. The shape of the detecting apparatus main body 1 is not particularly limited, but is preferably a rectangular parallelepiped (see FIG. 1). Note that the detecting apparatus main body 1 may have another shape (e.g., a prism such as a pentagonal prism or a column). The size of the detecting apparatus main body 1 is not particularly limited. For example, when the detecting apparatus main body 1 is in the shape of a rectangular parallelepiped (see FIG. 1), the length of the detecting apparatus main body 1 in the direction in which the cavity 2 extends (i.e., the exhaust gas flow direction) is preferably 1 to 30 mm, and the lengths of the two sides perpendicular to the longitudinal direction of the detecting apparatus main body 1 are preferably 0.5 to 10 mm and 10 to 50 mm, respectively.

Figure 6:
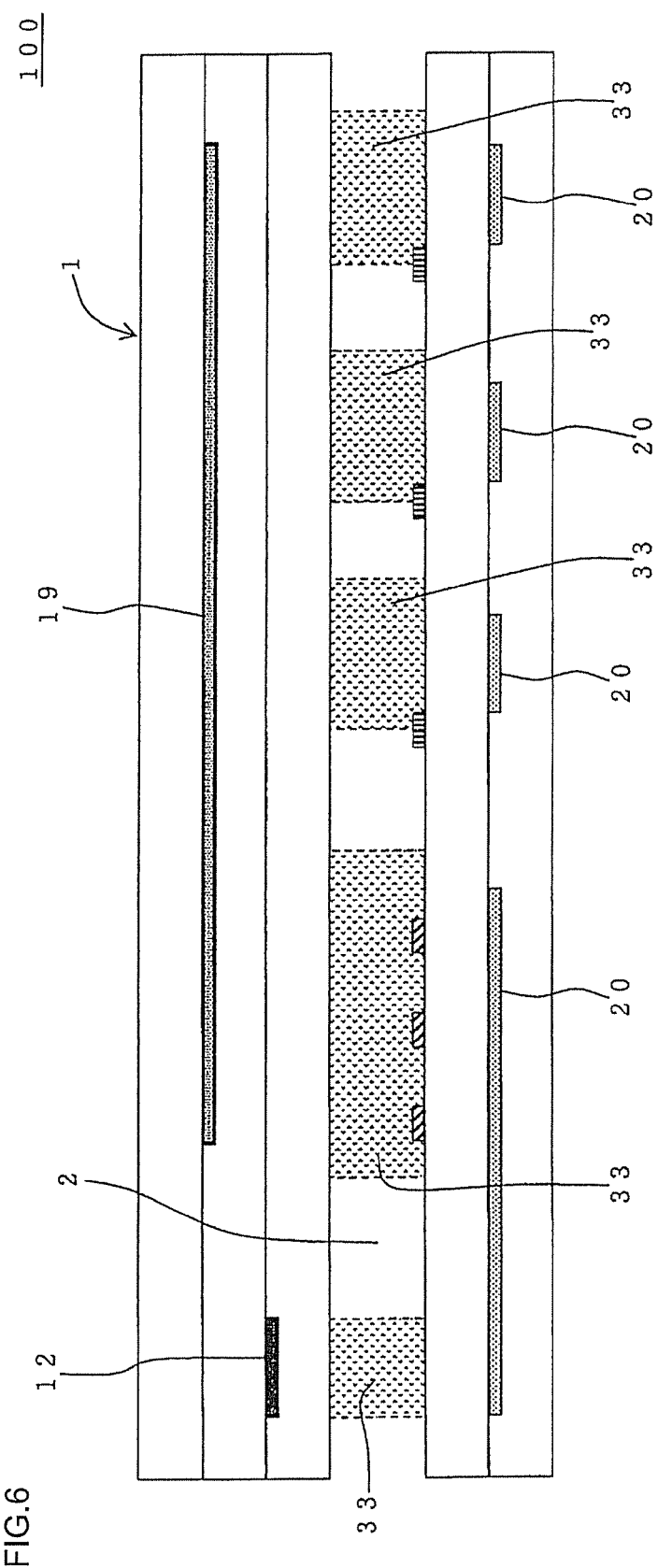
FIG. 6 is a cross-sectional view along the line A-A' shown in FIG. 2A, and shows a state in which plasma is generated during purification.

In the particulate matter detecting apparatus 100 according to this embodiment, as shown in FIG. 6, it is preferable that the detecting apparatus main body 1 include a purification electrode 19 and the ground electrode 11 (purification ground electrode 20) that are disposed so that the cavity 2 is positioned between the purification electrode 19 and the ground electrode 11, and a plasma 33 is generated inside the cavity 2 using the purification electrode 19 and the purification ground electrode 20 to remove the particulate matter that adheres to the inner wall surface of the cavity 2. It is preferable that the purification electrode 19 cover as wide a range of the cavity 2 between the inflow-side end 6 and the outflow-side end 7 as possible. It is preferable that the purification electrode 19 have a length corresponding to 70 to 99% of the length of the cavity 2 in the longitudinal direction. The dimension of the purification electrode 19 in the vertical direction in FIG. 2A (i.e., the vertical direction of the detecting apparatus main body 1) is not particularly limited, but is preferably larger than the dimension of the cavity 2 in the vertical direction of the detecting apparatus main body 1 (i.e., covers the entire cavity 2 in the vertical direction of the detecting apparatus main body 1), as shown in FIG. 2A. When generating the plasma 33 inside the cavity 2 to remove the particulate matter that adheres to the inner wall surface of the cavity 2 (see FIG. 6), the charging electrode 12 may be used as the purification electrode in addition to the purification electrode 19, and the charging ground electrode 13, the collection ground electrode 15, and the ion wind generation ground electrode 18 may be used as the purification ground electrode 20. Note that another purification ground electrode 18 may be added.

It is preferable that the purification electrode 19 and the purification ground electrode 20 contain at least one component selected from the group consisting of gold, silver, platinum, nickel, molybdenum, and tungsten. The content of these components is preferably 20 vol % or more.

The particulate matter detecting apparatus 100 according to this embodiment is particularly effective when the particulate matter that passes through the cavity 2 is soot discharged from a diesel engine or nanoparticles produced in a nanoparticle production plant.

A method of producing the particulate matter detecting apparatus 100 according to this embodiment is described below.

(Preparation of Forming Raw Material)

A ceramic raw material that contains at least one component selected from the group consisting of alumina, magnesium oxide, silicon oxide, silicon nitride, aluminum nitride, zirconia, a cordierite-forming raw material, mullite, spinel, a magnesium-calcium-titanium oxide, a barium-titanium-zinc oxide, and a barium-titanium oxide is mixed with other components to prepare a forming raw material slurry. The above-mentioned raw materials are preferable as the ceramic raw material. Note that the ceramic raw material is not limited thereto. As the components other than the ceramic raw material, it is preferable to use a binder, a plasticizer, a dispersant, water, and the like.

The binder is not particularly limited. An aqueous binder or a non-aqueous binder may be used. As the aqueous binder, methyl cellulose, polyvinyl alcohol, polyethylene oxide, or the like may be suitably used. As the non-aqueous binder, polyvinyl butyral, an acrylic resin, polyethylene, polypropylene, or the like may be suitably used. Examples of the acrylic resin include a (meth)acrylic resin, a (meth)acrylate copolymer, an acrylate-methacrylate copolymer, and the like.

The binder is preferably added in an amount of 3 to 20 parts by mass, and more preferably 6 to 17 parts by mass, based on 100 parts by mass of the ceramic raw material. If the binder is added in such an amount, cracks and the like can be prevented when forming the forming raw material slurry to produce a green sheet or when drying and firing the green sheet.

As the plasticizer, glycerol, polyethylene glycol, dibutyl phthalate, di(2-ethylhexyl) phthalate, diisononyl phthalate, or the like may be used.

The plasticizer is preferably added in an amount of 30 to 70 parts by mass, and more preferably 45 to 55 parts by mass, based on 100 parts by mass of the binder. If the amount of the plasticizer is more than 70 parts by mass, the resulting green sheet becomes too soft and may be deformed when processing the green sheet. If the amount of the plasticizer is less than 30 parts by mass, the resulting green sheet becomes too hard so that the handling capability may deteriorate (e.g., cracks may occur when merely bending the green sheet).

As the dispersant, an aqueous dispersant (e.g., anionic surfactant, wax emulsion, or pyridine) or a non-aqueous dispersant (e.g., fatty acid, phosphate, or synthetic surfactant) may be used.

The dispersant is preferably added in an amount of 0.5 to 3 parts by mass, and more preferably 1 to 2 parts by mass, based on 100 parts by mass of the ceramic raw material. If the amount of the dispersant is less than 0.5 parts by mass, the dispersibility of the ceramic raw material may decrease. As a result, the green sheet may produce cracks and the like. If the amount of the dispersant is more than 3 parts by mass, the amount of impurities may increase during firing although the dispersibility of the ceramic raw material remains the same.

The solvent is preferably added in an amount of 50 to 200 parts by mass, and more preferably 75 to 150 parts by mass, based on 100 parts by mass of the ceramic raw material.

The above-mentioned materials are sufficiently mixed using an alumina pot and alumina cobblestone to prepare a forming raw material slurry for forming a green sheet. The forming raw material slurry may be prepared by mixing the materials by ball milling using a mono ball.

The resulting forming raw material slurry is stirred under reduced pressure to remove bubbles, and the viscosity of the forming raw material slurry is adjusted to a predetermined value. The viscosity of the forming raw material slurry thus prepared is preferably 2.0 to 6.0 Pa·s, more preferably 3.0 to 5.0 Pa·s, and particularly preferably 3.5 to 4.5 Pa·s. The slurry can be easily formed into a sheet by adjusting the viscosity of the slurry within the above range. It may be difficult to form the slurry into a sheet if the viscosity of the slurry is too high or too low. The viscosity of the slurry refers to a value measured using a Brookfield viscometer.

(Forming)

The forming raw material slurry obtained by the above method is formed into a sheet to obtain a green sheet. The forming method it is not particularly limited insofar as a green sheet can be formed by forming the forming raw material into a sheet. A doctor blade method, a press forming method, a rolling method, a calendar roll method, or the like may be used. In this case, a green sheet for forming a cavity is also produced so that a cavity is formed when stacking the green sheets.

The thickness of the green sheet is preferably 50 to 800 μm.

The electrodes and lines are then disposed on the surface of the resulting green sheet. For example, when producing the particulate matter detecting apparatus shown in FIGS. 2A and 2B, it is preferable to print the electrodes and lines (not shown) at the corresponding positions of the green sheet so that the electrodes and lines are disposed at predetermined positions. In this case, a conductive paste for forming the electrodes and lines is prepared. The conductive paste may be prepared by adding a binder and a solvent (e.g., terpineol) to a powder that contains at least one component selected from the group consisting of gold, silver, platinum, nickel, molybdenum, and tungsten, and sufficiently kneading the mixture using a triple roll mill or the like. The conductive paste thus prepared is printed on the surface of the green sheet by screen printing or the like to form electrodes and lines having a predetermined shape.

The green sheets are then stacked. The green sheets are stacked so that the electrodes and the cavity are disposed as shown in FIGS. 2A and 2B. The green sheets are preferably stacked while applying a pressure.

(Firing)

The resulting green sheet laminate is dried at 60 to 150° C., and fired at 1200 to 1600° C. to obtain a particulate matter detecting apparatus. When the green sheet contains an organic binder, it is preferable to degrease the green sheet at 400 to 800° C. before firing.

EXAMPLES

The present invention is further described below by way of examples. Note that the present invention is not limited to the following examples.

Example 1

Preparation of Forming Raw Material

An alumina pot was charged with alumina (ceramic raw material), polyvinyl butyral (binder), di(2-ethylhexyl) phthalate (plasticizer), sorbitan trioleate (dispersant), and an organic solvent (xylene:butanol=6:4 (mass ratio)). The components were mixed to prepare a forming raw material slurry for forming a green sheet. 7 parts by mass of the binder, 3.5 parts by mass of the plasticizer, 1.5 parts by mass of the dispersant, and 100 parts by mass of the organic solvent were used based on 100 parts by mass of alumina.

The resulting forming raw material slurry was stirred under reduced pressure to remove bubbles, and the viscosity of the forming raw material slurry was adjusted to 4 Pa·s. The viscosity of the slurry was measured using a Brookfield viscometer.

(Forming)

The forming raw material slurry obtained by the above method was formed into a sheet using a doctor blade method. A green sheet for forming a cavity was also produced so that a cavity was formed when stacking the green sheets. The thickness of the green sheet was 250 μm.

Electrodes and lines were formed on the surface of the resulting green sheet. A conductive paste for forming the electrodes and lines was prepared by adding 2-ethylhexanol (solvent), polyvinyl butyral (binder), di(2-ethylhexyl) phthalate (plasticizer), sorbitan trioleate (dispersant), alumina (green sheet common material), and a glass frit (sintering aid) to a platinum powder, and sufficiently kneading the mixture using a kneading machine and a triple roll mill (platinum:alumina:glass frit:2-ethylhexanol:polyvinyl butyral:di(2-ethylhexyl) phthalate:sorbitan trioleate=80:15:5:50:7:3.5:1 (mass ratio)). The conductive paste thus prepared was screen-printed on the surface of the green sheet to form electrodes and lines having a predetermined shape.

The green sheets were stacked under pressure using a heating-type uniaxial press machine to obtain an unfired body of a particulate matter detecting apparatus shown in FIGS. 2A and 2B.

(Firing)

The green sheet laminate (unfired body of particulate matter detecting apparatus) thus obtained was dried at 120° C., and fired at 1500° C. to obtain a particulate matter detecting apparatus. The resulting particulate matter detecting apparatus was in the shape of a rectangular parallelepiped having dimensions of 0.6 cm×1.0 cm×3.2 cm. The shape of the cross section of the cavity perpendicular to the exhaust gas flow direction was rectangular (0.2 cm×0.5 cm).

(Particulate Matter Measurement)

The particulate matter measuring apparatus was installed in an apparatus provided with an oxidizing catalyst and a defective DPF disposed in an exhaust pipe of a diesel engine. The particulate matter measuring apparatus was disposed on the downstream side of the DPF. A direct injection diesel engine (displacement: 1400 cc) was used as the diesel engine. An exhaust gas with a different PM concentration (0.5 to 20.2 mg/m$^3$) was discharged at an engine speed of 2000 rpm while changing the exhaust gas recirculation (EGR) rate. The operation state was switched between a particulate matter detection state and a cavity purification state in a cycle of 10 seconds while discharging the exhaust gas from the diesel engine. When detecting particulate matter, a pulse wave at a voltage of 3 kV and a current of 1 mA was applied to the charging electrode. A wave at a voltage of 2 kV and a current of 1 mA were applied to the collection electrode to measure a change in capacitance between the electrodes due to collection of particulate matter. A rectangular wave at a voltage of 5 kV and a current of 3 mA was applied to the ion wind generation electrode to generate an ion wind (volume: 5 l/s) inside the cavity. When purifying the inner wall surface of the cavity, the charging ground electrode, the collection ground electrode, and the ion wind generation ground electrode were used as the purification ground electrode. A pulse wave at a voltage of 4 kV and a current of 5 mA was applied between the purification electrode and the purification ground electrode to generate a plasma inside the cavity. The particulate matter adhering to the inner wall surface of the cavity was thus oxidized and purified.

From the measurement results, the relationship "P=0.485×ΔC+1.023" (approximate straight line) was observed between a change ΔC (pF) in capacitance and a PM concentration P (mg/m$^3$) measured using a smoke meter (manufactured by AVL, model: "4158"). The correlation between the change ΔC in capacitance and the PM concentration P was indicated by r$^2$=0.98. It was confirmed that the PM concentration can be detected by measuring a change in capacitance. Note that r indicates the Pearson product-moment correlation coefficient.

INDUSTRIAL APPLICABILITY

The particulate matter detecting apparatus can be suitably used to immediately detect defects (i.e., abnormality) of a DPF. This makes it possible to contribute to preventing air pollution.

The invention claimed is:

1. A particulate matter detecting apparatus comprising:
a detecting apparatus main body having a cavity that is formed through the detecting apparatus main body;
a particle charging section that can charge particulate matter that has entered the cavity through one end of the cavity;
a collection section that can collect the particulate matter charged by the particle charging section and measure the amount of the particulate matter; and
an ion wind generation section that allows the particulate matter charged by the particle charging section to flow toward the other end of the cavity,
wherein the particle charging section, the collection section, and the ion wind generation section are provided inside the cavity in this order from said one end, and
wherein the detecting apparatus main body includes a purification electrode and a purification ground electrode that are disposed so that the cavity is positioned between the purification electrode and the purification ground electrode, and a silent discharge can be generated inside the cavity using the purification electrode and the purification ground electrode to remove the particulate matter that adheres to the inner wall surface of the cavity.

2. The particulate matter detecting apparatus according to claim 1,
wherein the detecting apparatus main body includes a charging electrode and a charging ground electrode that are disposed so that the particle charging section provided inside the cavity is positioned between the charging electrode and the ground electrode; and
wherein the particle charging section charges the particulate matter via the silent discharge that is generated inside the cavity using the charging ground electrode.

3. The particulate matter detecting apparatus according to claim 1,
wherein the detecting apparatus main body includes a charging electrode and a charging ground electrode that are disposed so that the particle charging section provided inside the cavity is positioned between the charging electrode and the charging ground electrode; and
wherein the particle charging section charges the particulate matter via a corona discharge that is generated inside the cavity using the charging electrode.

4. The particulate matter detecting apparatus according to claim 2,
wherein the charging electrode and the charging ground electrode contain at least one component selected from the group consisting of gold, silver, platinum, nickel, molybdenum, and tungsten.

5. The particulate matter detecting apparatus according to claim 1,
wherein the collection section includes a collection electrode that can electrostatically collect the particulate matter charged by the particle charging section and is disposed on an inner wall surface of the cavity.

6. The particulate matter detecting apparatus according to claim 5,
wherein the collection electrode included in the collection section is a plate-shaped electrode that has an external profile provided with elevations or depressions.

7. The particulate matter detecting apparatus according to claim 5,
wherein the collection electrode contains at least one component selected from the group consisting of gold, silver, platinum, nickel, molybdenum, and tungsten.

8. The particulate matter detecting apparatus according to claim 5, further comprising a collection ground electrode that is disposed inside a wall that forms the inner wall surface of the cavity on which the collection electrode is disposed, the particulate matter detecting apparatus being capable of measuring the amount of the particulate matter collected by the collection electrode by detecting a change in capacitance between the collection electrode and the collection ground electrode.

9. The particulate matter detecting apparatus according to claim 8,
wherein the collection ground electrode contains at least one component selected from the group consisting of gold, silver, platinum, nickel, molybdenum, and tungsten.

10. The particulate matter detecting apparatus according to claim 5, further comprising:
at least one electrode extension portion that is disposed in the inner wall surface of the collection section on which the collection electrode is disposed so as not to come in contact with the collection electrode,
wherein the collection electrode and the electrode extension portion are electrically connected when the particulate matter collected by the collection electrode has accumulated between the collection electrode and the electrode extension portion.

11. The particulate matter detecting apparatus according to claim 10, comprising:
a plurality of the electrode extension portions,
wherein the plurality of electrode extension portions differ in distance from the collection electrode.

12. The particulate matter detecting apparatus according to claim 1,
wherein the ion wind generation section includes an ion wind generation electrode on the inner wall surface of the cavity, the ion wind generation electrode causing a surface discharge so that the particulate matter charged by the particle charging section moves toward the outflow-side end.

13. The particulate matter detecting apparatus according to claim 1,
wherein the ion wind generation section includes an ion wind generation electrode on the inner wall surface of the cavity, the ion wind generation electrode causing a corona discharge so that the particulate matter charged by the particle charging section moves toward the outflow-side end.

14. The particulate matter detecting apparatus according to claim 12,
wherein the ion wind generation electrode contains at least one component selected from the group consisting of gold, silver, platinum, nickel, molybdenum, stainless steel, and tungsten.

15. The particulate matter detecting apparatus according to claim 1,
wherein a material that forms the detecting apparatus main body is a ceramic.

16. The particulate matter detecting apparatus according to claim 15,
wherein the detecting apparatus main body is formed by stacking a plurality of ceramic tapes.

17. The particulate matter detecting apparatus according to claim 15,
wherein the ceramic that forms the detecting apparatus main body contains at least one component selected from the group consisting of alumina, magnesium oxide, silicon oxide, silicon nitride, aluminum nitride, zirconia, cordierite, mullite, spinel, a magnesium-calcium-titanium oxide, a barium-titanium-zinc oxide, and a barium-titanium oxide.

18. The particulate matter detecting apparatus according to claim 1,
wherein the purification electrode and the purification ground electrode contain at least one component selected from the group consisting of gold, silver, platinum, nickel, molybdenum, and tungsten.

19. The particulate matter detecting apparatus according to claim 1,
wherein the particulate matter that passes through the cavity is soot discharged from a diesel engine or nanoparticles produced in a nanoparticle production plant.

* * * * *